United States Patent
Ho

(10) Patent No.: US 9,308,086 B2
(45) Date of Patent: Apr. 12, 2016

(54) METHOD AND SYSTEM FOR BALLOON COUNTERPULSATION DURING AORTIC VALVE REPLACEMENT

(75) Inventor: Paul C. Ho, Honolulu, HI (US)

(73) Assignee: HOCOR Cardiovascular Technologies LLC, Honolulu, HI (US)

( * ) Notice: Subject to any disclaimer, the term of this patent is extended or adjusted under 35 U.S.C. 154(b) by 243 days.

(21) Appl. No.: 13/227,276

(22) Filed: Sep. 7, 2011

(65) Prior Publication Data

US 2012/0116439 A1     May 10, 2012

Related U.S. Application Data

(60) Provisional application No. 61/384,989, filed on Sep. 21, 2010.

(51) Int. Cl.
*A61M 29/00* (2006.01)
*A61F 2/24* (2006.01)
(Continued)

(52) U.S. Cl.
CPC .......... *A61F 2/2427* (2013.01); *A61B 17/1204* (2013.01); *A61B 17/12118* (2013.01);
(Continued)

(58) Field of Classification Search
CPC .................. A61B 17/12027; A61B 17/12036; A61B 17/1204; A61B 17/12122; A61B 17/12136; A61B 2017/00703; A61B 2017/00783; A61B 2017/22065; A61B 2017/22067; A61B 17/12031; A61B 17/12045; A61B 17/12109; A61B 17/12118; A61F 2/2433; A61M 1/10; A61M 1/106; A61M 1/1063; A61M 1/1065; A61M 1/107; A61M 1/1072; A61M 1/1074; A61M 1/3607; A61M 1/3613; A61M 25/10; A61M 25/1018; A61M 2025/1015; A61M 2230/04
USPC ........ 606/191–192, 194; 604/914; 600/16–18
See application file for complete search history.

(56) References Cited

U.S. PATENT DOCUMENTS 4,077,394 A      3/1978   Mccurdy
5,295,995 A *    3/1994   Kleiman ................ 606/194
(Continued)

FOREIGN PATENT DOCUMENTS

EP            0230996 A2     8/1987
WO       WO 00/47139 A1     8/2000
(Continued)

OTHER PUBLICATIONS

International search report and written opinion dated Dec. 23, 2011 for PCT Application No. US2011/50883.
(Continued)

*Primary Examiner* — David C Eastwood
*Assistant Examiner* — Martin T Ton
(74) *Attorney, Agent, or Firm* — Wilson, Sonsini, Goodrich & Rosati

(57) ABSTRACT

Methods and systems for regulating aortic regurgitation during aortic valve replacement or repair procedures utilize a temporary aortic valve (TAV) catheter and a controller. The temporary aortic valve catheter has an expandable occlusion device which can partially occlude the aortic lumen during ventricular diastole with a lesser occlusion during ventricular systole. Exemplary balloon structures include multiple, independently inflatable balloons which are inflated in synchrony with the cardiac cycle by the controller. By controlling aortic regurgitation, the repair or replacement protocols can be conducted with less interference from blood flow.

16 Claims, 9 Drawing Sheets

(51) Int. Cl.
*A61B 17/12* (2006.01)
*A61B 17/00* (2006.01)
*A61M 25/10* (2013.01)

(52) U.S. Cl.
CPC . *A61B17/12136* (2013.01); *A61B 2017/00703* (2013.01); *A61F 2250/0059* (2013.01); *A61M 25/1011* (2013.01)

(56) References Cited

U.S. PATENT DOCUMENTS

| | | | |
|---|---|---|---|
| 5,413,558 A | | 5/1995 | Paradis |
| 5,486,192 A * | | 1/1996 | Walinsky et al. ............. 606/194 |
| 6,989,027 B2 | | 1/2006 | Allen et al. |
| 7,927,268 B1 * | | 4/2011 | St. Germain et al. ........... 600/18 |
| 2004/0116951 A1 * | | 6/2004 | Rosengart .................... 606/167 |
| 2006/0052867 A1 | | 3/2006 | Revuelta et al. |
| 2007/0112422 A1 * | | 5/2007 | Dehdashtian ................ 623/2.11 |
| 2008/0147160 A1 | | 6/2008 | Ghione et al. |
| 2009/0030503 A1 | | 1/2009 | Ho |
| 2009/0030510 A1 * | | 1/2009 | Ho ............................... 623/2.11 |
| 2009/0082609 A1 * | | 3/2009 | Condado .......................... 600/4 |
| 2010/0094209 A1 | | 4/2010 | Drasler et al. |

FOREIGN PATENT DOCUMENTS

| | | |
|---|---|---|
| WO | WO 2007/100410 A2 | 9/2007 |
| WO | WO 2008/051554 A2 | 5/2008 |

OTHER PUBLICATIONS

Mishra, et al. Role of prophylactic intra-aortic balloon pump in high-risk patients undergoing percutaneous coronary intervention. Am J Cardiol. Sep. 1, 2006;98(5):608-12. Epub Jun. 30, 2006.

Vandenberghe, et al. In Vitro Testing of a Temperary Catherter-Based Aortic 'Parachute' Valve. ASAIO Journal 2008, v. 54, 574-577.

European search report dated Nov. 6, 2013 for EP Application No. 09800932.7.

European search report and search opinion dated Feb. 20, 2015 for EP Application No. 11827209.5.

* cited by examiner

METHOD AND SYSTEM FOR BALLOON COUNTERPULSATION DURING AORTIC VALVE REPLACEMENT

CROSS REFERENCE TO RELATED APPLICATIONS

This application claims the benefit under 35 U.S.C. 119 of U.S. Provisional Patent Application No. 61/384,989, filed Sep. 21, 2010, the full disclosure of which is incorporated herein by reference.

BACKGROUND OF THE INVENTION

1. Field of the Invention

The present invention relates generally to medical devices and methods. More particularly, the present invention relates to a method and system for facilitating percutaneous aortic valve replacement.

Patients suffering from significant aortic valve disease are frequently treated by aortic valve replacement procedures. While most aortic valve replacements are still performed in open chest procedures, recently there have been significant advances in minimally invasive aortic valve replacement where the valve is introduced through either a transapical approach (minimally invasive) or a transvascular (percutaneous) approach over the aortic arch.

Both transapical and transvascular PAV procedures are "beating heart" procedures where continuing blood flow from the left ventricle into the aorta creates hemodynamic forces on the replacement valves and the tools used in the replacement procedures. In an effort to control the hemodynamic forces and to stabilize the tools and valve used for replacement, that the use of a "temporary aortic valve" (TAV) has recently been proposed. As described in commonly owned published US Patent Applications US 2009/0030503 and US 2009/0030510, the full disclosures of which are incorporated herein by reference, a catheter is intravascularly introduced over the aortic arch to position a balloon assembly in the ascending aorta just above the Sinus of Valsalva. The balloon assembly includes three equally sized balloons disposed in parallel about the distal tip of the catheter, and the inflated balloons together limit retrograde blood flow (flow in the direction from the aorta toward the aortic valve) during diastole, thus limiting disturbance of the tools and/or valves located in the aortic valve annulus during the procedure. The balloon inflation only partially occludes the aortic lumen in order to both allow antegrade flow during systole and to permit a limited retrograde flow during diastole in order to perfuse the coronary vasculature through the Sinus of Valsalva and to protect the left ventricle from excessive volume overload.

While of great potential benefit, the use of the balloon structures described in the prior patent applications is necessarily a compromise between resistance to regurgitation during diastole and forward blood flow patency through the aorta during systole. Also, the balloon structures and protocols described in the published patent applications do not provide for adjusting the extent of occlusion of the aorta as may be optimal during different stages of the valve removal and replacement procedures.

For these reasons, it would be desirable to provide methods and systems for occluding the aorta to limit aortic regurgitation during valve repair and replacement procedures where the degree of aortic occlusion can be adjusted during the procedure, both in synchronizing with the systolic and diastolic portions of the heartbeat and during different segments of the procedure, such as valve ablation, valve removal, replacement valve positioning, replacement valve assembly, and the like. At least some of these objectives will be met by the inventions described herein below.

2. Description of the Background Art

US Patent Publications US 2009/0030503 and US 2009/0030510 have been described above. The use of an intra-aortic balloon pump during coronary interventions on patients having complicated left main stenoses is described in Mishra, et al., (2006) Am J Cardiol 98:608-612. U.S. Patent Publication US 2008/0147160 describes a catheter having an expandable cage structure located in the Sinus of Valsalva for stabilizing a guide wire in transapical valve replacement procedures. The use of a "parachute" valve for providing a temporary aortic valve is described in Vandenberghe, et al., (2008) ASAIO J 54:547-577.

BRIEF SUMMARY OF THE INVENTION

The present invention provides methods and systems for regulating aortic regurgitation during aortic valve replacement and/or repair procedures. As used herein, "aortic regurgitation" refers to the retrograde flow of blood back from the aorta toward the aortic valve during ventricular diastole. In replacement/repair procedures where the native aortic valve leaflets are prevented from closing or excised, retrograde flow through the valve annulus can interfere with the procedure and potentially harm the patient.

The present invention provides a variable occlusion device which is positioned in the ascending aorta just above the Sinus of Valsalva to control regurgitation during diastole while allowing less impeded antegrade blood flow to the aorta from the left ventricle during systole. In addition, as described in more detail below, the present invention will permit a controlled level of retrograde flow (regurgitation) from the aorta during diastole in order to perfuse the coronary arteries which is necessary to maintain the health of the heart during beating heart procedures.

While controlled retrograde flow during ventricular diastole can be provided by fixed, partial occlusion devices positioned in the ascending aorta above the Sinus of Valsalva, as described in commonly owned applications US 2009/0030503 and US 2009/0030510, the present invention provides for variable occlusion of blood flow through the aorta so that the degree or level of occlusion can be selected and changed during different portions of the cardiac cycle (systole and diastole) as well as during different portions of the procedure, e.g., valve ablation, valve excision, prosthetic valve implantation, etc. Thus, for example, during ventricular diastole, the percentage of aortic luminal occlusion can be maximized to limit regurgitation through the aortic valve annulus while providing a sufficient level of coronary artery perfusion through the Sinus of Valsalva. During ventricular systole, in contrast, the percentage of occlusion of the aortic lumen will be lessened considerably. While some small level of occlusion will be present due to the cross-sectional area of the catheter and/or other tool which is holding the occlusion device, it is theoretically possible to reduce the additional occlusion provided by the variable occlusion device to a level close to zero. While such minimal occlusion is desirable to maximize antegrade flow through the aorta, it will usually be desirable to maintain balloons or other expandable elements in order to stabilize the catheter or other tool access (resulting in a finite but acceptable level of resistance to antegrade flow).

Methods according to the present invention for regulating aortic regurgitation during aortic valve replacement or repair procedures comprise positioning a catheter or other tool having a variable occlusion device in the ascending aorta above the Sinus of Valsalva. The occlusion device is expanded to partially occlude the aortic lumen during ventricular diastole to inhibit aortic regurgitation while allowing perfusion of the coronary arteries via the Sinus of Valsalva. During ventricular systole, however, the occlusion device is partially or fully contracted in order to reduce occlusion of the aortic lumen and lessen inhibition of antegrade blood flow from the left ventricle to the aorta. Expansion and contraction of the occlusion device is typically continued in synchrony with the cardiac cycle (diastole followed by systole) while the repair or replacement procedure is performed.

The extent of expansion of the occlusion device during ventricular diastole is selected to optimize perfusion of the coronary arteries via the Sinus of Valsalva while limiting regurgitation toward or through the aortic annulus. It will be appreciated that whether aortic regurgitation actually occurs will also depend on what is happening in the aortic annulus during the repair or replacement procedure. For example, if a balloon or other structure is expanded within the aortic annulus, that balloon or other structure may completely prevent retrograde flow through the annulus. Perfusion of the coronary arteries via the Sinus of Valsalva, however, should continue regardless of what steps are being performed in the repair or replacement procedure.

The degree of occlusion of the aorta during ventricular diastole will preferably be at least 40%, usually in the range of 40% to 90% and more usually from 50% to 90% of the cross-sectional area of the aortic lumen where the occlusion device is present. In contrast, the percentage occlusion provided by the occlusion device (including the cross-sectional area of the catheter or other device which carries the occlusion device) during ventricular systole will be less than the occlusion provided during ventricular diastole. Usually, the occlusion of the aortic lumen during ventricular systole will be no greater than 75%, usually being no greater than 65%, and often being no greater than 25%. While there is no upper limit on the patency of the aortic lumen during ventricular systole (ideally there would be no occlusion), there will usually be some occlusion resulting from both the cross-sectional area of the catheter or other supporting device and, particularly in the case of inflatable balloons, the presence of two, three, or more balloons which are inflated about the catheter in order to stabilize the catheter during ventricular systole where the ejected blood can destabilize the catheter or other tool.

The occlusion device could have any one of many structural manifestations. For example, the occlusion could have an expandable scaffold with a plurality of one-way valve structures where individual ones of the valve structures could be separately controlled to allow opening and closing at desired portions of the cardiac cycle. More usually, however, the occlusion device will comprise at least one inflatable element or structure, typically comprising multiple, separately inflatable structures, e.g., "balloons." Such inflatable balloons are generally preferred as they are widely used in cardiovascular devices and procedures and allow for highly reliable performance with minimum risk to the patient. Moreover, the balloons themselves can be made in a variety of ways in order to provide for different structural mechanical attributes. For example, the balloons may be distensible (usually elastomeric) or non-distensible, may have circular cross-sections or non-circular cross-sections, can be separately inflated or inflated through common manifolds in order to inflate and deflate groups of balloons simultaneously, and the like. While certain specific balloon constructions will be described and illustrated in detail below, it should be appreciated that other balloon and mechanical structures would be suitable (although perhaps less preferable) for performing the methods and providing the systems of the present invention.

Catheter positioning will usually be achieved intravascularly over the aortic arch. Introduction of a catheter over the aortic arch, in turn, can be accomplished using conventional techniques, e.g., introduction of a catheter by the Seldinger technique or via a surgical cut down into the femoral artery in the groin. Alternatively, the catheter used to position the variable occlusion device of the present invention could be introduced percutaneously through the apex of the heart, referred to as a "transapical" approach. In such cases, the catheter would pass through the aortic valve before reaching the ascending aortic through the Sinus of Valsalva. Generally, however, intravascular approaches are preferred over transapical approaches. In addition, catheters used for intravascularly positioning the occlusion device over the aortic arch can also be used for introducing catheters and other tools for repairing or replacing the aortic valve, as described in more detail below. In particular, the transaortic catheters can be used for advancing the replacement valve through a lumen in the catheter, typically while the catheter remains stabilized by continued balloon expansion in the ascending aorta. In addition, the transaortic catheters can be used for introducing tools for ablating, removing, or otherwise preparing the native aortic valve for the repair or replacement procedure, as well as for introducing tools for manipulating and expanding the replacement aortic valve.

Systems according to the present invention comprise a catheter having an expandable and contractible occlusion device near its distal end. The catheter is adapted to be introduced into the aorta, and the occlusion device is sized to partially occlude the ascending aorta above the Sinus of Valsalva when fully expanded. An inflation controller is connectable to the catheter to alternatively (1) expand the occlusion device during ventricular diastole to inhibit aortic regurgitation while allowing perfusion of the coronary arteries via the Sinus of Valsalva and (2) to contract or reduce the size of the occlusion device during ventricular systole to lessen inhibition of antegrade blood flow from the left ventricle to the aorta. The systems will typically further include a sensor to detect ventricular diastole and ventricular systole. For example, a heart rhythm monitor (EKG) may be provided to detect ventricular diastole and systole. Alternatively, a pressure sensor may be provided in the system, typically on or near a distal end of the catheter, to detect ventricular diastole and systole based on pressure in the ascending aorta or elsewhere in the vasculature.

The occlusion device on the catheter will be sized, when fully expanded during diastole, to occlude to at least 40% of the aortic lumen area where positioned, usually occluding from 40% to 90%, and often from 50% to 90%. The degree or amount of occlusion when the occlusion device is fully or partially deflated during systole will be much less, never being above 75% of the aortic lumen area, usually being less than 65% and preferably being below 25% of the lumen area.

The occlusion device may have any of the various structures described above with respect to the method of the present invention. In particular, it may comprise one or more inflatable elements, typically comprising a plurality of independently inflatable elements, where the inflation controller inflates and deflates certain ones of the plurality of elements simultaneously. Alternatively, the inflation controller may inflate and deflate individual ones of the plurality of inflatable elements independently. Usually, the inflation controller will maintain inflation of one or more elements at all times during the procedure in order to stabilize the position of the catheter in the ascending aorta.

DETAILED DESCRIPTION OF THE INVENTION

Figure 1:
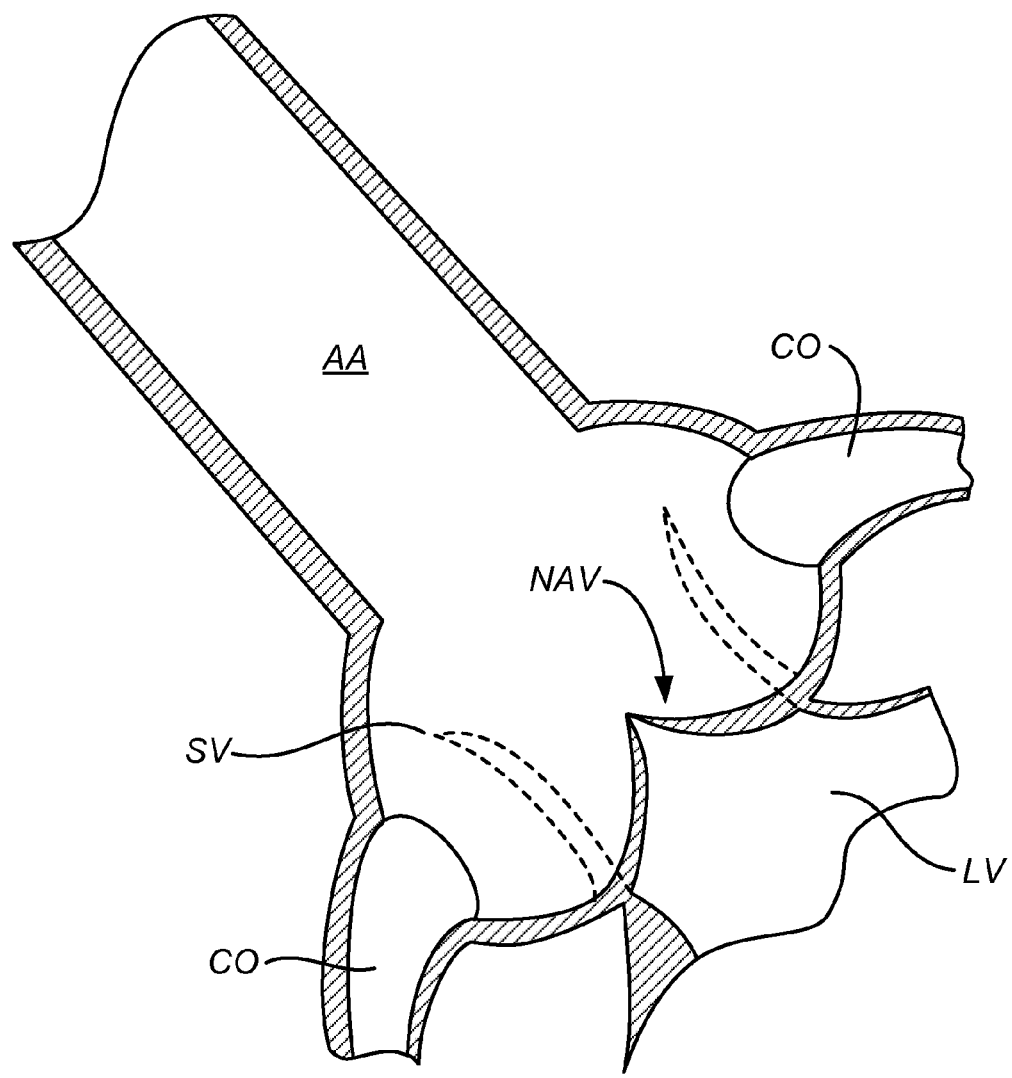
FIG. 1 is a schematic illustration of a native aortic valve and the surrounding tissue structures including the ascending aortic, the Sinus of Valsalva, and the coronary ostium leading to the coronary arteries.

A native aortic valve (NAV) is illustrated in FIG. 1. The native aortic valve is positioned just below the ascending aorta (AA) and the Sinus of Valsalva (SV). Coronary ostia (CO) branch off from the Sinus of Valsalva and provide perfusion to coronary arteries which feed the heart muscle (not illustrated). Beneath the native aortic valve is the left ventricle, and the aortic valve is closed during diastole (as shown in full line in FIG. 1) and opens during systole (shown in broken line in FIG. 1) when the left ventricle contracts and ejects blood from the ventricle into the aorta.

Figure 2:
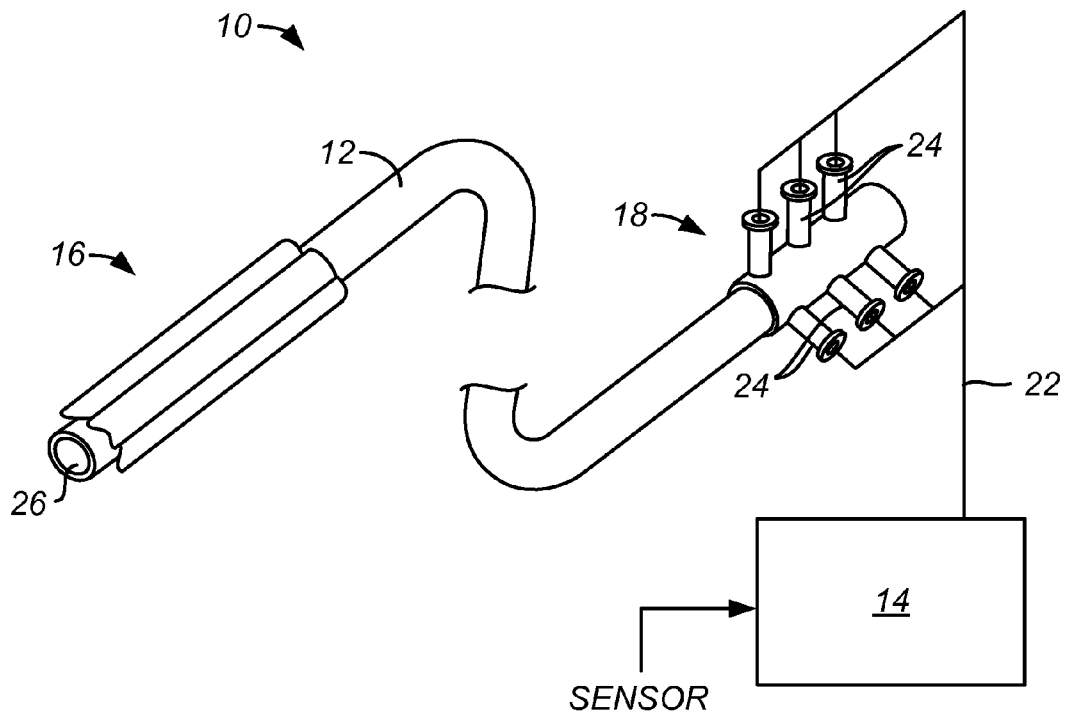
FIG. 2 illustrates a system constructed in accordance with the principles of the present invention including a temporary aortic valve (TAV) catheter and system controller.
Figure 2A:
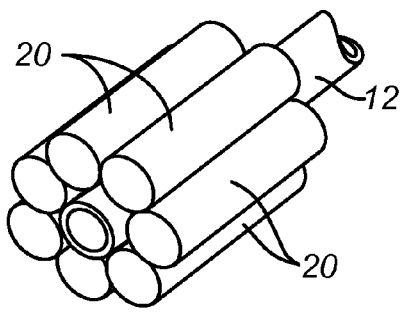
FIG. 2A illustrates a multiple-balloon structure present at a distal end of the catheter of the system in FIG. 2 with all balloons inflated.
Figure 2B:
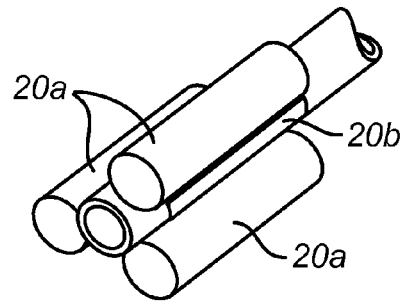
FIG. 2B is similar to FIG. 2A showing the configuration when every other balloon is deflated.

Referring to FIG. 2, a system 10 for regulating aortic regurgitation according to the present invention comprises a temporary aortic valve (TAV), catheter 12 and a controller 14. The catheter 12 has a balloon structure 16 at or near its distal end and an inflation hub 18 at or near its proximal end. In the illustrated embodiment, the balloon structure 16 includes six identical cylindrical balloons disposed coaxially and symmetrically about the body of the catheter 12. FIG. 2A illustrates individual balloons 20 of the balloon structure 16, with all the individual balloons being inflated. FIG. 2B is similar to FIG. 2A, except that only three of the balloons 20a are inflated while three other balloons 20b (only one of which can be seen in FIG. 2B) are deflated.

The system controller 14 will provide for balloon inflation, typically providing at least one inflation tube or conduit 22 which is connected to the hub 18. Optionally, individual branches of the inflation conduit 22 can be manifolded into a plurality of inflation connectors 24 on the inflation hub 18. It will be appreciated that internal valving within the controller 14 and/or the hub 18 may allow for selective inflation of individual ones and/or individual groups of the balloons 20 of the balloon structure 16.

The controller 14 will typically also receive input from a sensor which provides information regarding the cardiac cycle, usually providing information on the transition between ventricular systole and diastole so that the individual ones of the balloons may be inflated and deflated depending on the status of the cardiac cycle, as described in more detail below. The sensor (not illustrated) may be an EKG attached externally to the patient or may be a pressure sensor located on the catheter 12 itself. The controller 14 may be set to inflate and deflate the selected balloons during every cardiac cycle (a 1:1 duty cycle) or every other cardiac cycle (a 1:2 duty cycle) or every third cardiac cycle (a 1:3 duty cycle) or every "nth" cardiac cycle (a 1:n duty cycle, n typically being from 1 to 10) for the best hemodynamic response based on cardiac output, blood pressure, pulse rate, and the like.

The TAV catheter will usually have dimensions and physical properties compatible with introducing the catheter over the aortic arch so that the balloon structure 16 may reside within the ascending aorta just above the Sinus of Valsalva. Usually, the catheter 12 will have a tubular body with a large central lumen 26 which may be utilized to provide access to the aortic valve during replacement and repair procedures. The catheter 12 will also usually include individual or common lumens providing for inflation of the individual balloons 20. These lumens may be provided, for example, within the wall of the body of catheter 12 and formed during extrusion (not illustrated). Other conventional means for providing balloon inflation lumens may also be utilized.

Figure 3A:
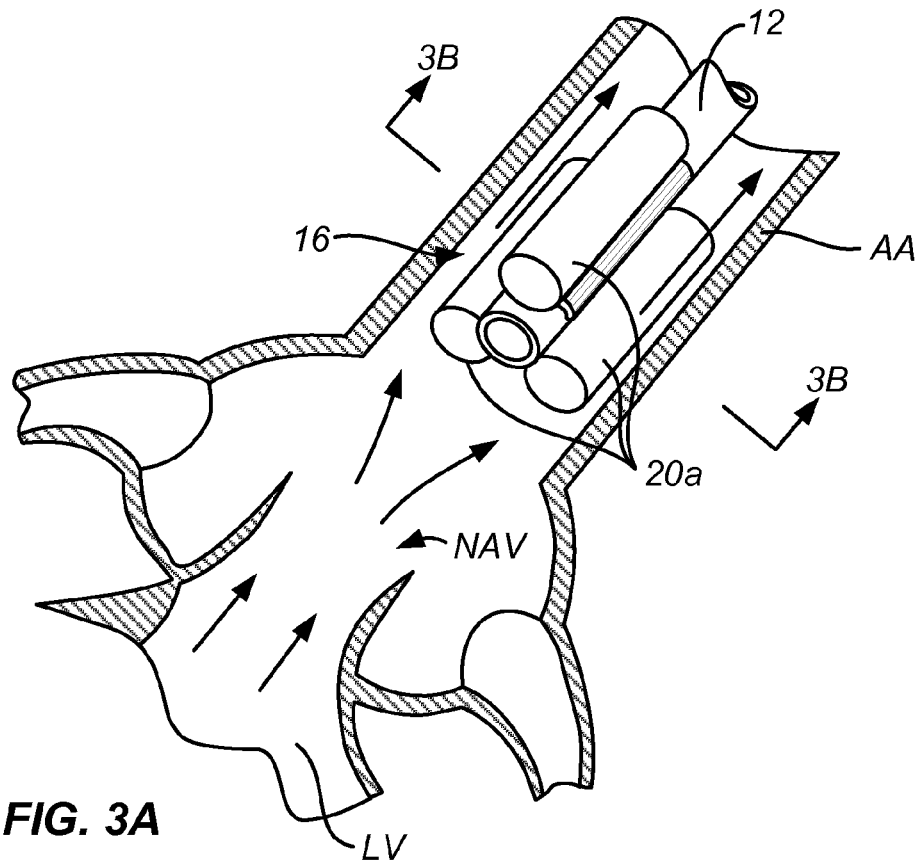
FIG. 3A illustrates the catheter of the system of FIG. 2 positioned in an ascending aorta during systole.
Figure 3B:
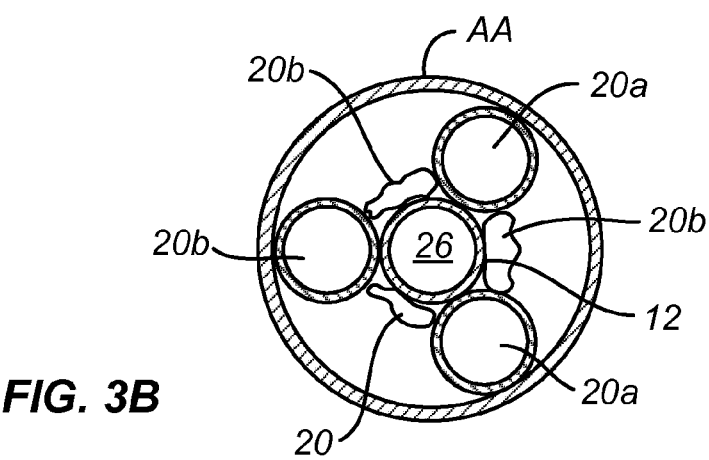
FIG. 3B is a cross-sectional view taken along line 3B-3B of FIG. 3A.

Referring now to FIGS. 3A and 3B, the catheter 12 may be positioned over the aortic arch so that the balloon structure 16 lies in the ascending aorta. By inflating selected balloons 20a while leaving the other balloons deflated during systole, blood may be ejected from the left ventricle (LV) through the open native aortic valve (NAV) during systole so that blood flows past the balloon structure 16 with the deflated balloons decreasing flow resistance.

Figure 4A:
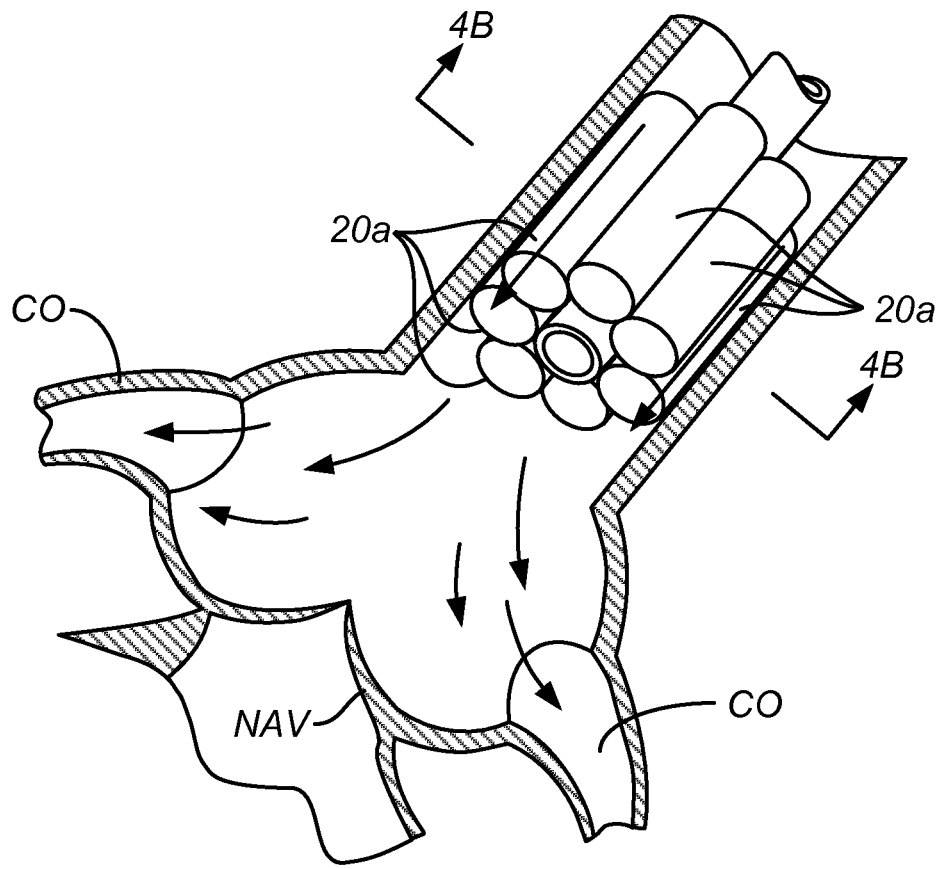
FIG. 4A illustrates the catheter of the system of FIG. 2 positioned in an ascending aorta during diastole.
Figure 4B:
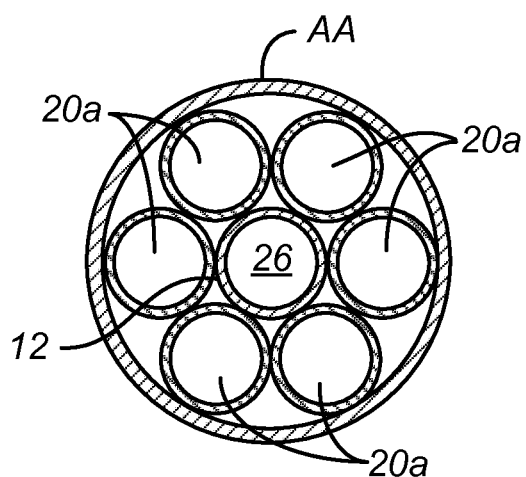
FIG. 4B is a cross-sectional view taken along line 4B-4B of FIG. 4A.

Referring now to FIGS. 4A and 4B, the balloon structure 16 will have all balloons 20a inflated during diastole in order to limit retrograde flow while still permitting perfusion of the coronary arteries through the coronary ostia. While the native aortic valve (NAV) shown in FIGS. 3A and 3B and in FIGS. 4A and 4B is quite healthy, it will be appreciated that the TAV catheters of the present invention will be used during replacement procedures where the valve is unhealthy to begin with (likely subject to significant stenosis and/or regurgitation) and that the purpose of the variable occlusion is to control regurgitation while the valve is being treated and, at many points during the procedure, where the valve annulus is fully or partially open without any active valve mechanism.

Figure 5A:
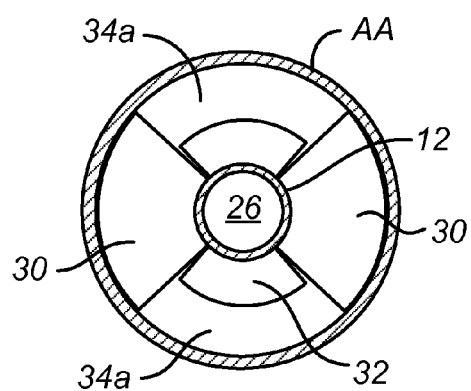
FIGS. 5A and 5B illustrate an alternative balloon configuration with the balloons fully inflated in FIG. 5A and partially inflated in FIG. 5B.
Figure 5B:
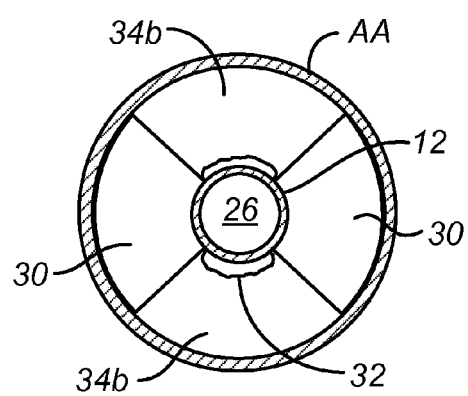

While the balloons 20 of the balloon structure 16 of TAV catheter 12 are shown as cylindrical with symmetric placement about the catheter, it will be appreciated that a wide variety of other balloon numbers, configurations, and inflation patterns may be utilized. For example, as shown in FIG. 5A, it may be possible to employ four pie-shaped balloons, with two larger balloons 30 and two smaller balloons 32. When the balloons are fully inflated, as shown in FIG. 5A the smaller balloons leave flow channels 34a bypassing the balloon structure. The size of the flow passages 34a will be selected to be compatible with the desired retrograde flow of regurgitation during diastole. In contrast, the smaller balloons 32 may be deflated, as shown in FIG. 5B to provide much larger flow passages 34b, to be utilized during systole.

Figure 6A:
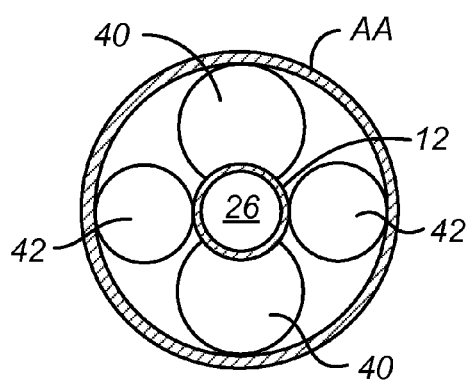
FIGS. 6A and 6B illustrate an alternative balloon configuration with the balloons fully inflated in FIG. 6A and partially inflated in FIG. 6B.
Figure 6B:
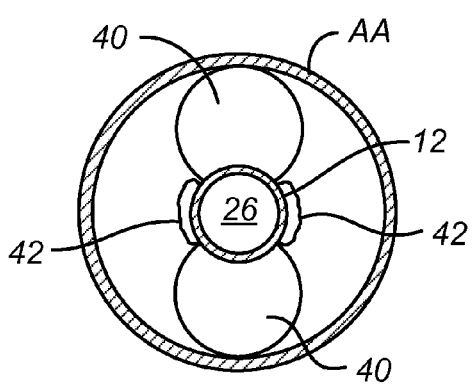

Similarly, as shown in FIGS. 6A and 6B, cylindrical balloons may have different geometries and different sizes. Two larger cylindrical balloons 40 are disposed on opposed sides of the catheter 12 while two smaller cylindrical balloons 42 are disposed between the larger balloons 40 and on opposed sides of the catheter 12. The smaller balloons 42 may be inflated (as shown in FIG. 6A) during diastole and deflated (as shown in FIG. 6B) during systole (as shown in FIG. 6B). Usually, the larger balloons 40 will remain inflated at all times in order to stabilize the catheter 12 during the replacement or repair protocol.

Figure 7A:
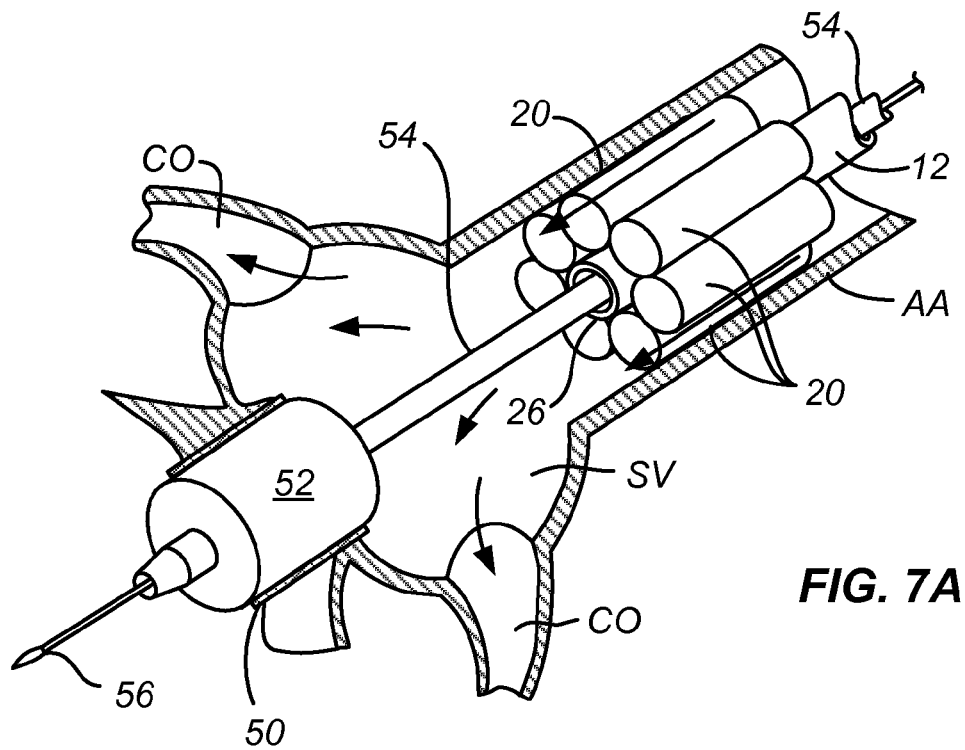
FIGS. 7A-7F illustrate use of the catheter of the system of FIG. 1 for ablating and replacing a native aortic valve with a percutaneous aortic valve (PAV) in accordance with the present invention.

Referring now to FIGS. 7A through 7F, an exemplary aortic valve replacement procedure which utilizes the TAV catheter 12 of the present invention will be described. As shown in FIG. 7A, the TAV catheter 12 is placed in the ascending aorta (AA) over the aortic arch (not shown) via an intravascular procedure. After predilation with a balloon, an ablation stent 50 is placed within the native aortic valve by inflating a balloon 52 carried by a catheter 54 introduced through the lumen 26 of the catheter 12. The stent 50 is used to open and/or ablate the native valve in a generally conventional manner. During the ablation procedure, the balloons 20 will be selectively expanded and contracted as described previously. As shown in FIG. 7A, the balloons 20 are fully inflated to minimize retrograde flow while allowing adequate perfusion of the coronary arteries through the coronary ostia (CO), as shown by the arrows in FIG. 7A. It will be appreciated that the balloons will inflate and deflate during the procedure regardless of the inflation or deflation of balloon 52 or other balloons as utilized later in the procedure.

Figure 7B:
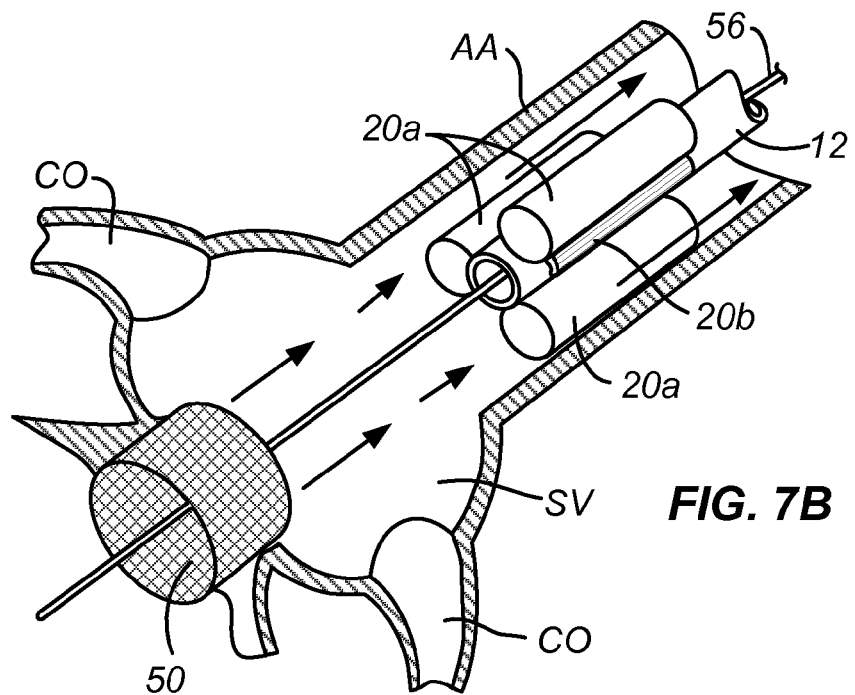

Referring now to FIG. 7B, the catheter 54 carrying balloon 52 has been removed with the stent 50 being left in place. At this point in the procedure, the stent 50 is fully opened and, were it not for the balloon structure 16 on catheter 12, the aortic annulus and left ventricle would be exposed to uncontrolled regurgitation of blood from the aorta during diastole. As shown in FIG. 7B, however, the selected balloons 20b are deflated during systole so that blood may flow from the left ventricle, through the stent 50 in the direction of the arrows past the deflated balloons. It will be appreciated, however, that during the next cycle of diastole, the balloons 20b will reinflate, as shown in FIG. 7A, to limit the retrograde flow and aortic regurgitation while permitting sufficient retrograde flow to perfuse the coronary arteries via the coronary ostia (CO).

Figure 7C:
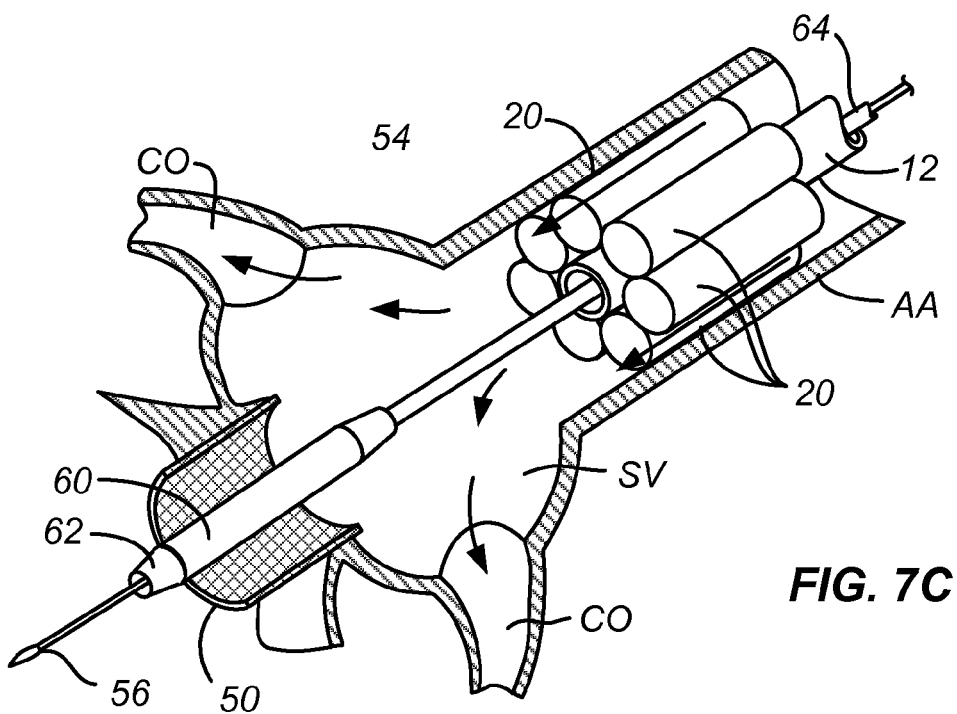

Referring now to FIG. 7C, the next stage of the valve replacement protocol is introducing the percurtaneous aortic valve (PAV) 60 using a second catheter 64 having a balloon 62. As shown in FIG. 7C, the heart is in ventricular diastole, and the blood is flowing past the fully inflated balloons 20 and perfusing the coronary arteries through the coronary ostia (CO). As soon as the heart enters systole, the balloons 20b will deflate, as shown for example in FIG. 7B.

Figure 7D:
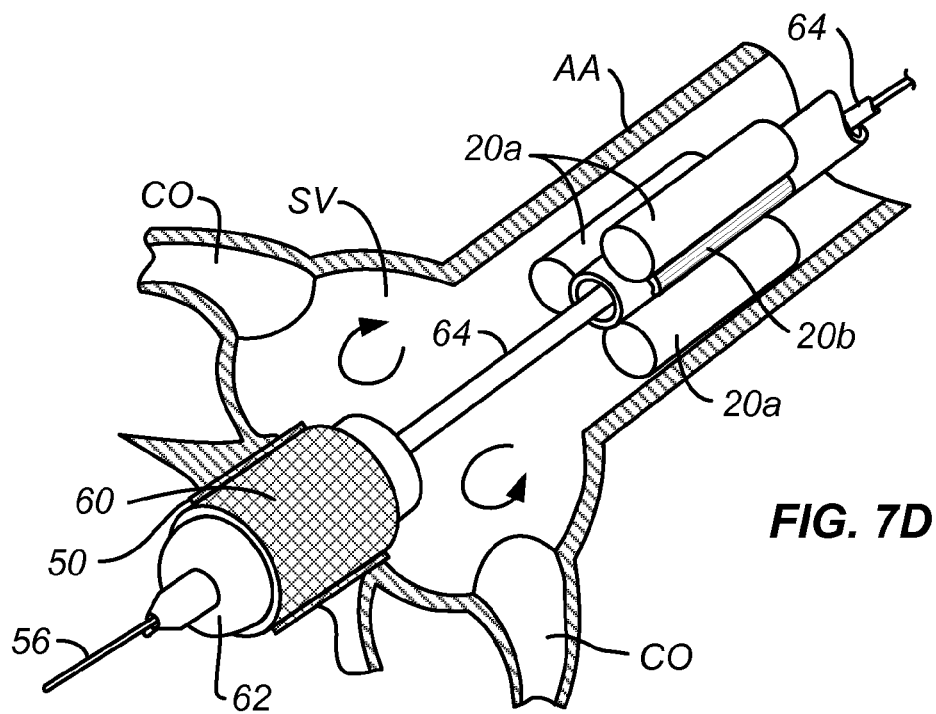

Referring now to FIG. 7D, the balloon 62 is inflated to deploy the PAV 60 within the previously placed stent 50. As illustrated in FIG. 7D, the heart is in systole but the inflation of balloon 62 prevents blood from flowing from the left ventricle through the aortic annulus. Thus, blood will remain temporarily still within the Sinus of Valsalva since the heart, during systole, inhibits flow of blood into the coronary arteries.

Figure 7E:
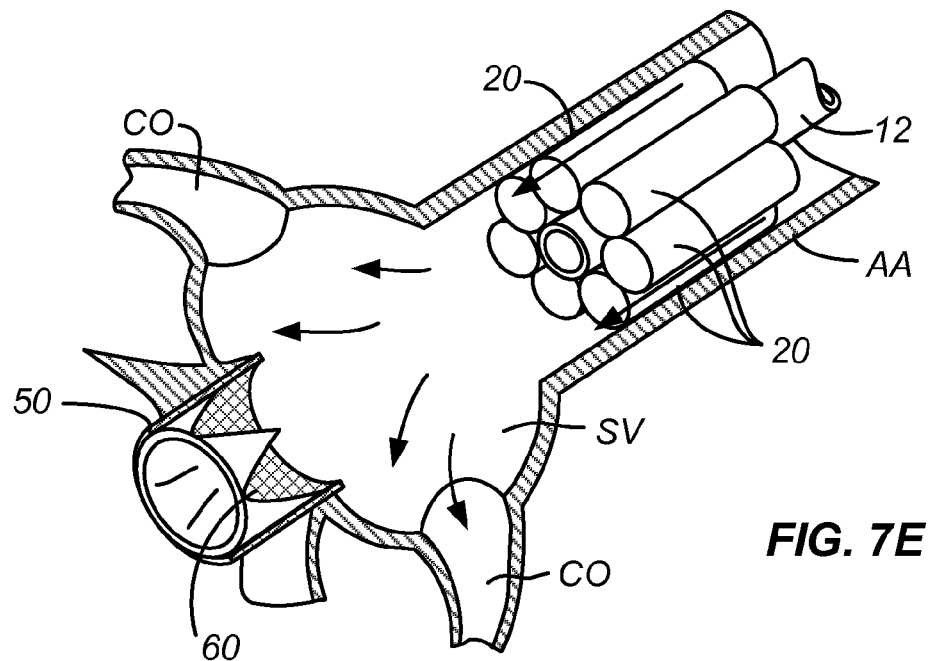

Referring now to FIG. 7E, after the PAV 60 has been deployed, the catheter 64 carrying balloon 62 will be removed leaving the TAV catheter 12 temporarily in place. As the heart is in diastole, the retrograde flow past fully inflated balloons 20 will occur and will perfuse the coronary arteries via the coronary ostia (CO). The PAV leaflets, however, will be closed preventing valve regurgitation.

Figure 7F:
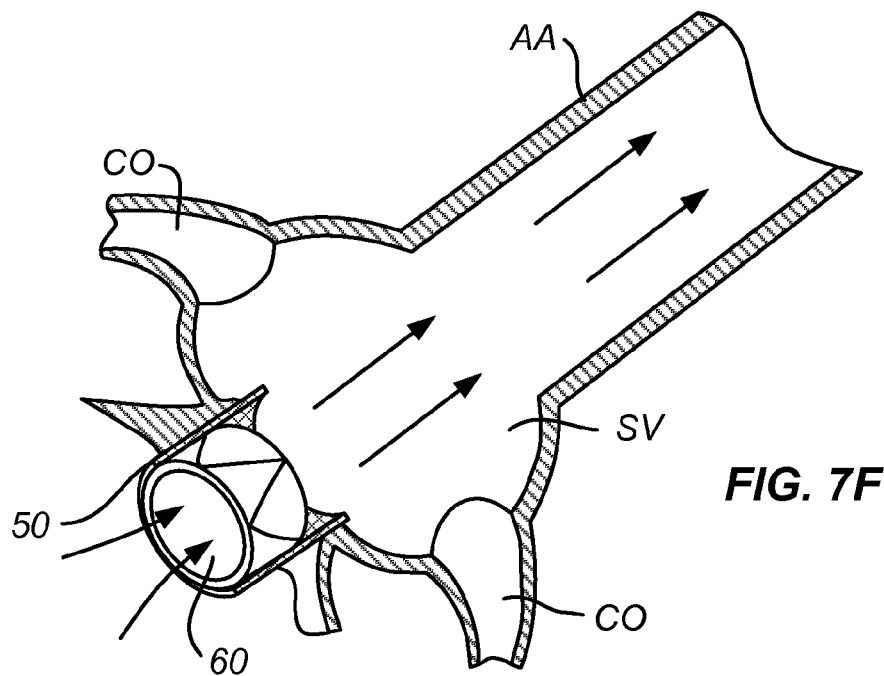

Finally, as shown in FIG. 7F, the TAV catheter 12 is removed leaving the PAV 60 to function in a normal manner. In FIG. 7F, the heart is shown in systole with blood flow through the open leaflets of the valve. As soon as the heart enters ventricular diastole, however, the valve leaflets of valve 60 will close and prevent regurgitation.

Calculations

Figure 8:
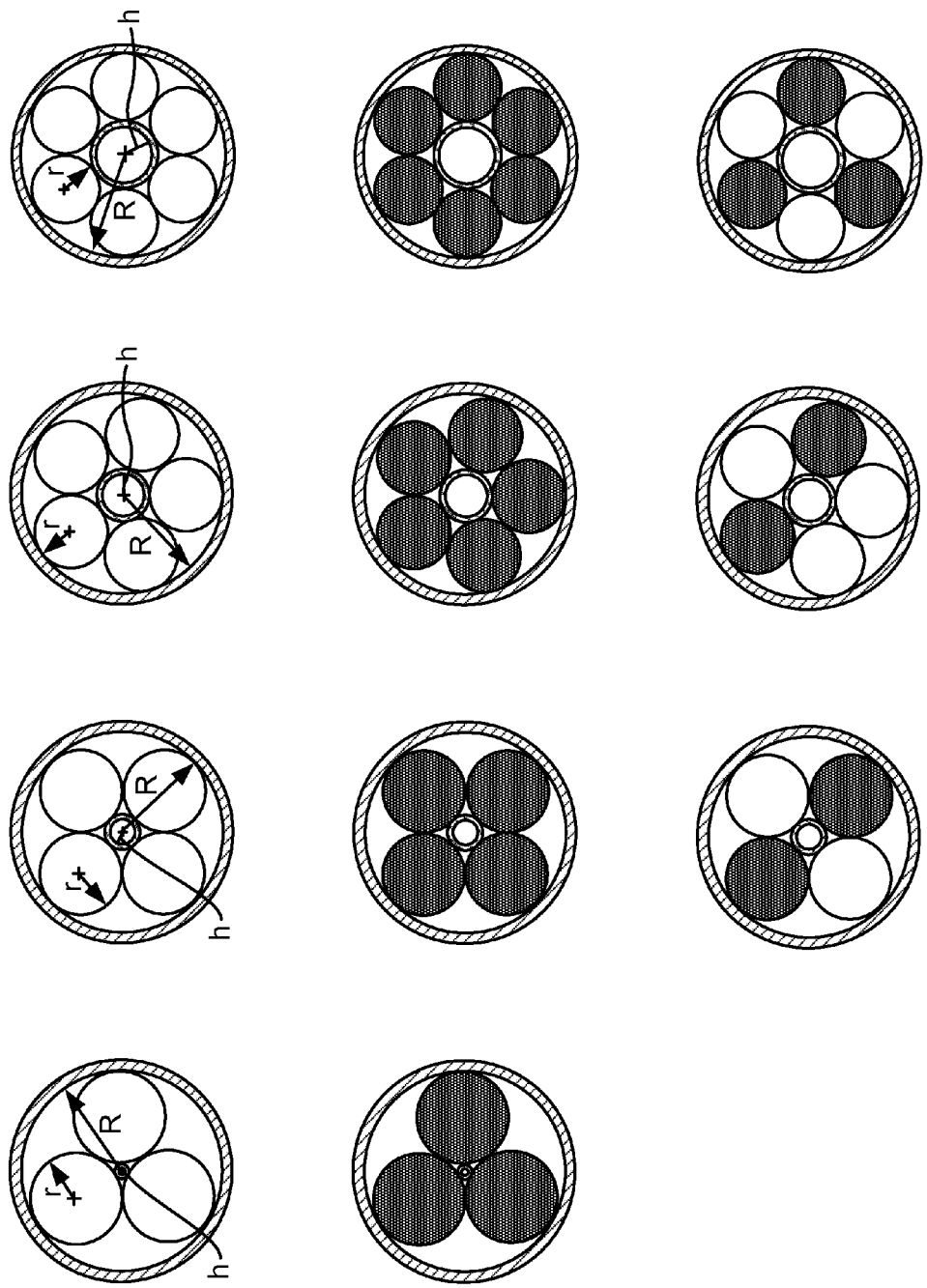
FIG. 8 illustrates certain balloon configurations which are analyzed in the Calculations section herein below.

To quantify the gap-to-balloon relationships which produce effective mild-to-moderate range aortic stenosis and insufficiency of the temporary aortic valve, mathematical calculations are performed on TAV models comprising three to six balloons of the same sizes surrounding a central catheter (FIG. 8). The choice of using the same size balloons is to ease calculation and manufacturing complexities, though it is not a requirement as long as the resultant cross-section are of the gap:overall luminal aorta ratios are between the target range of 25 to 60%. Hence, balloons of various sizes and configurations (non-circular) may be design options in future developments.

The potential benefits of balloon counterpulsation to further unload the temporary valve's effective stenosis, various balloon counterpulsation permutations are explored as shown (FIG. 8). Balloon counterpulsation is defined as balloon inflation during diastole and balloon deflation during systole similar to the timing cycle of the intra-aortic balloon pump. (Safian and Feed, *Intra-aortic Balloon Counterpulsation*, Manual of Interventional Cardiology $3^{rd}$ Ed., royal Oak, Mich., Physicians' Press, pp 146-147). During TAV balloon counterpulsation, certain configurations may be potentially mechanically less stable such as when all of the balloons counterpulsate and may lead to some catheter instability (fling or wobble). Unstable configurations, such as single or double balloon counterpulsation in the three-balloon TAV, three balloon counterpulsation in the four-balloon TAV, three-balloon counterpulsation in the five-balloon TAV and four-balloon counterpulsation in the six-balloon TAV, are not considered in he calculations.

TAV permutations considered in the calculations are the following: counterpulsation of all of the TAV balloons (the middle row of FIG. 8), counterpulsation of the catercorner balloons in the four-balloon TAV (the remaining two as fixed supportive balloons), counterpulsation of the two opposing balloons in the five-balloon TAV (three remaining fixed supporting balloons) and counterpulsation of every other balloon in the six-balloon TAV (others as fixed support balloons) (the bottom row of FIG. 8).

Results

Table 1 (top row) shows the relationship between the radius of the aorta (R) to the radius of the TAV balloons (r) and the radius of the central catheter (h) for the 3-, 4-, 5- and 6-balloon TAV configurations. As first reported in the original TAV study, the 3-balloon TAV cross-sectional gap area:total area of the ascending aorta is calculated to be approximately 35%, which falls in the moderate range effective aortic stenosis and insufficiency during systole and diastole, respectively. As the number of balloons surrounding the central catheter increases, the balloon size becomes smaller as demonstrated by the increasing R:r ratio. Furthermore, as the balloon size becomes smaller, the center space becomes larger allowing for a larger lumen central catheter to be housed as shown by the decreasing R:h ratio. In the 4-balloon configuration, the diastolic gap area:total area ratio is lowered to 28% compared to the 3-balloon TAV's 35%, which decreases the effective aortic insufficiency. As the number of balloons increases to 5 and 6, the respective diastolic gap area:total area ratio is further lowered to 25% and 22%. While the effective TAV aortic insufficiency decreases with increasing number of balloons, the effective aortic stenosis can increase to beyond critical range (gap:total area <25%) in the 5- and 6-balloon TAV. This would entail less effective aortic insufficiency by the TAV which may or may not be adequate for coronary perfusion during diastole, however, during systole the TAV's effective aortic stenosis will become significant.

TABLE 1

Comparative TAV Configurations with Fixed (Inflated without Counterpulsation) Balloons

| Dimensional Relationship | 3-Balloon TAV | 4-Balloon TAV | 5-Balloon TAV | 6-Balloon TAV |
|---|---|---|---|---|
| R:r ratio | R = 2.15 r | R = 2.41 r | R = 2.70 r | R = 3.0 r |
| R:h ratio | R = 14.29 h | R = 5.88 h | R = 3.85 h | R = 3.0 h |
| Gap:Area | 35% | 28% | 25% | 22% |
| TAV's Effective AS | Moderate | ↑ | ↑↑ | ↑↑↑ |
| TAV's Effective AI | Moderate | ↓ | ↓↓ | ↓↓↓ |
| Estimated Central Catheter Size | 7-FR. | 17-FR. | 26-FR. | 32-FR. |

The central catheter diameter is dependent on the size of the ascending aorta (as indicated by the R:h ratio) as well as the number of TAV balloons (Table 1). For average size adult human ascending aorta, the central catheter-TAV can conceptually be fabricated to be as small as a 7-French system to as excessively large as 30-French or greater. Tables 2A and 2B show the effects of balloon counterpulsation when all (Table 2A) or some (Table 2B) of the TAV balloons are inflated-deflated timed to the cardiac cycle as described. When the TAV balloons are deflated during systole and inflated during diastole via balloon counterpulsation, it can alleviate or lower the degree of effective aortic stenosis while keeping the controlled effective aortic insufficiency unchanged. When all of the balloons of the TAV counterpulsate, the effective aortic stenosis is significantly reduced to negligible to very mild ranges as shown in Table 2A. In the 4-balloon configured TAV, counterpulsation of two selective catercorner balloons while keeping the other two as fixed support decreases the effective aortic stenosis during systole to a gap area:total area ratio of 62.7%, as compared to 28% without counterpulsation. Similar improvement in the systole effective aortic stenosis is seen in the five- and six-balloon TAV with selective balloon counterpulsation as noted in Table 2B, with the systole gap area:total area of 52.1% and 55.6%, respectively. Note that balloon counterpulsation is most relevant in the five- and six-balloon configurations where the effective aortic stenosis is at critical values. Hence, balloon counterpulsation appears to present a unique advantage over the fixed-balloon TAV system.

TABLE 2A

Counterpulsation with All of the Balloons

| Dimensional Relationship | 3-Balloon TAV | 4-Balloon TAV | 5-Balloon TAV | 6-Balloon TAV |
|---|---|---|---|---|
| Gap:Area (systole) | 99% | 97% | 93% | 88% |
| Gap:Area (diastole) | 35% | 28% | 25% | 22% |
| TAV's Effective AS (systole) | Negligible | Negligible | Very Mild | Very Mild |
| TAV's Effective AI (diastole) | Moderate | Moderate (same as fixed) | Mild-Moderate (same as fixed) | Mild (same as fixed) |

TABLE 2B

Counterpulsation with Selected Balloons

| Dimensional Relationship | 3-Balloon TAV | 4-Balloon TAV | 5-Balloon TAV | 6-Balloon TAV |
|---|---|---|---|---|
| Gap:Area (systole) | — | 62.7% | 52.1% | 55.6% |
| Gap:Area (diastole) | 35% | 28% | 25% | 22% |
| TAV's Effective AS (systole) | Moderate | Mild | Mild | Mild |
| TAV's Effective AI (diastole) | Moderate | Moderate (same as fixed) | Mild-Moderate (same as fixed) | Mild (same as fixed) |

These calculations demonstrate the design potential to manipulate and control the TAV's effective aortic stenosis and insufficiency by varying the number of balloons used to create the TAV and by adding balloon counterpulsation to lessen the systolic effective TAV stenosis. From the design standpoint, there are a variety of ways to create the optimal gap:total cross-sectional area ratio for the desirable effective TAV stenosis and insufficiency via non-circular vs. circular balloons, non-uniform vs. uniform balloons and non-balloon structures. The initial choice of using balloons of the same size in each TAV is to simplify mathematical modeling and manufacturing process. The choice of using inflatable balloons in the TAV is for its ease of deployment and removal.

As the number of balloons increases in a given size ascending aorta, the size of the balloons will decrease as clearly demonstrated by the R to r ratio. The relationship between R and h will also influence the size of catheter used. Furthermore, the distance between the balloons and the center of the ascending aorta will also increase as the number of balloons increases. Hence, with more balloons in the TAV, there will be a larger space in the center of the ascending aorta to house a larger central catheter. In the fixed balloon TAV permutations, the effective aortic stenosis increases as the number of balloons increases, while the effective aortic insufficiency decreases accordingly. The TAV model permutations may allow for opportunity for catheter size fitting or tailoring based on the aortic size, the number of balloons on the TAV and the associated hemodynamic profile.

In the five- and six-balloon TAVs, the systolic effective aortic stenosis reaches critical range of 25%, which is unacceptable in the replacement of severe aortic stenosis procedure. In these cases, balloon counterpulsation appears mandatory to alleviate the excessive TAV stenosis during systole. Also in the five- and six-balloon TAV configurations, the effective aortic insufficiency during diastole lowers toward mild range which is fabulous in preventing excessive regurgitation and congestive heart failure but could limit adequate coronary perfusion. The follow-on animal studies will be able to determine the relationship between the degree of TAV's effective insufficiency and diastole coronary filling.

With the addition of balloon counterpulsation, it is found that the TAV's effective aortic stenosis during systole can be significantly reduced, while the effective aortic insufficiency during diastole is unchanged. For all of the balloon configurations used in the calculations (three-, four-, five- and six-balloon TAVs), the systolic effective aortic stenosis is reduced to negligible ranges (when all balloons counterpulsate) to mild ranges (when selective balloons counterpulsate). This reduction in antegrade blood flow obstruction can further help to stabilize the patient during the percutaneous aortic valve replacement procedure. This is particularly true for the five- and six-balloon TAVs where the effective aortic stenosis is already in the critical range in the fixed balloon models. The tremendous relief of effective TAV stenosis by counterpulsating all of the balloons is impressive, but is at the least partially offset by the increased potential for catheter instability (fling or wobble) which must be considered and mitigated in the final design. Counterpulsating selective alternating balloons can unload the effective TAV stenosis, while the stationary balloons can continue to serve as catheter support/anchor during the entire valve replacement procedure.

These calculations represent conceptual permutations of the original TAV design provided in U.S. 2009/0030503 and U.S. 2009/0030510 as an evaluation to optimize its function as mechanical and hemodynamic support for the percutaneous aortic valve replacement procedure. The presented mathematical calculations are limited to idealized models where the balloons stay circular, the ascending aorta has a circular circumference free of atherosclerotic irregularities, perfect contacts between balloons and the aortic wall without slippage, leakage or resonance vibrations. In reality, the balloon compliance may encroach upon the gaps, creating more than expected contacts with the aortic wall, and the gap:total cross-sectional area ratio may further be altered by the irregular aortic profile from disease conditions. Excessive and/or inadequate TAV-aortic wall contacts can occur. Animal validations along with the theoretical model analyses are vital in developing TAV system into a successful supportive device in PAVR.

In conclusion, the ability to adjust and improve the TAV's function is possible by varying the number and/or geometry of the balloons utilized and implementing balloon counterpulsation. Optimized of device configurations will also depend on other factors such as the desirable guide catheter size and the required TAV hemodynamic profiles. The TAV balloon counterpulsation should not be confused with IABP counterpulsation in that the balloon volume of the TAV is significantly less (30-40 cc in IABP vs. <3 cc in TAV) without full aortic occlusion and should be safe to use with the presence of aortic insufficiency. Similar to the hemodynamic support of IABP in high-risk percutaneous coronary interventions, however, the TAV can provide additional hemodynamic support to optimize patient safety and procedural outcome in PAVR.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for regulating aortic regurgitation, said method comprising:

positioning a catheter comprising a tubular body and a variable occlusion device in the ascending aorta above the sinus of valsalva, the variable occlusion device comprising first and second expandable occlusion elements disposed in parallel about the tubular body;

expanding the first and second occlusion elements to partially occlude the aortic lumen about the tubular body of the catheter during ventricular diastole to inhibit aortic regurgitation while allowing perfusion of the coronary arteries via the sinus of valsalva;

contracting the first occlusion element while the second occlusion element remains expanded to reduce occlusion of the aortic lumen during ventricular systole to lessen inhibition of blood flow from the left ventricle to the aorta;

performing a replacement or repair procedure while alternating expanding and contracting the first occlusion element in synchrony with diastole and systole as the second occlusion element remains expanded.

2. A method as in claim 1, wherein the occlusion device is expanded to occlude from 40% to 90% of the aortic lumen during ventricular diastole and is contracted to reduce occlusion to below 75% of the aortic lumen during ventricular systole.

3. A method as in claim 2, wherein the occlusion device is contracted to reduce occlusion below 65% during ventricular systole.

4. A method as in claim 3, wherein the occlusion device is contracted to reduce occlusion below 50% during ventricular systole.

5. A method as in claim 4, wherein the occlusion device is contracted to reduce occlusion below 25% during ventricular systole.

6. A method as in claim 2, wherein one or more of the first or second occlusion element of the variable occlusion device comprises at least one inflatable element.

7. A method as in claim 2, wherein one or more of the first or second occlusion element of the variable occlusion device comprises a plurality of independently inflatable elements.

8. A method as in claim 7, wherein the plurality of inflatable elements are inflated and deflated simultaneously.

9. A method as in claim 7, wherein individual ones of the elements are inflated while other ones of the elements are deflated.

10. A method as in claim 7, wherein at least some elements remain inflated at all times to stabilize the occlusion device position within the ascending aorta.

11. A method as in claim 1, wherein positioning the catheter comprises advancing the catheter over the aortic arch.

12. A method as in claim 1, wherein positioning the catheter comprises advancing the catheter transapically.

13. A method as in claim 1, wherein performing the replacement or repair comprises advancing a replacement valve through a lumen of the catheter.

14. A method as in claim 1, further comprising removing the native valve, wherein expanding and contracting the occlusion device continues after the valve has been removed.

15. A method as in claim 1, wherein the first and second occlusion elements are disposed in parallel about a distal end of the catheter.

16. A method as in claim 1, wherein the first and second occlusion elements are disposed symmetrically about a distal end of the catheter.

* * * * *